US00PP14293P29

(12) United States Plant Patent
Hoek

(10) Patent No.: US PP14,293 P2
(45) Date of Patent: Nov. 11, 2003

(54) CHRYSANTHEMUM PLANT NAMED 'ANASTASIA YELLOW'

(50) Latin Name: *Chrysanthemum X morifolium*
Varietal Denomination: Anastasia Yellow

(75) Inventor: Jan Hoek, 's-Gravenzande (NL)

(73) Assignee: Deliflor Chrysanten B.V., Maasdijk (NL)

( * ) Notice: Subject to any disclaimer, the term of this patent is extended or adjusted under 35 U.S.C. 154(b) by 0 days.

(21) Appl. No.: 10/232,888

(22) Filed: Aug. 31, 2002

(51) Int. Cl.[7] ..... A01H 5/00
(52) U.S. Cl. ..... Plt./289
(58) Field of Search ..... Plt./289, 287, 288

*Primary Examiner*—Bruce R. Campell
*Assistant Examiner*—June Hwu
(74) *Attorney, Agent, or Firm*—C. A. Whealy

(57) ABSTRACT

A new and distinct cultivar of Chrysanthemum plant named 'Anastasia Yellow', characterized by its large quilled spider double-type inflorescences with yellow-colored ray florets; numerous ray florets and few inconspicuous disc florets; dark green-colored foliage; strong and upright flowering stems; low number of lateral branches; short response time; and excellent postproduction longevity.

1 Drawing Sheet

Botanical classification/cultivar designation: *Chrysanthemum×morifolium* cultivar Anastasia Yellow.

BACKGROUND OF THE INVENTION

The present invention relates to a new and distinct cultivar of Chrysanthemum plant, botanically known as *Chrysanthemum×morifolium* and referred to by the name 'Anastasia Yellow'.

The new Chrysanthemum was discovered and selected by the Inventor in a controlled environment in 's-Gravenzande, The Netherlands, as a naturally-occurring whole plant mutation of the Chrysanthemum cultivar Anastasia, disclosed in U.S. Plant Pat. No. 13,550. The new plant was discovered within a population of plants of the cultivar Anastasia and was selected on the basis of its unique yellow-colored ray florets.

Asexual reproduction of the new Chrysanthemum by terminal cuttings harvested in 's-Gravenzande, The Netherlands since November 2001, has shown that the unique features of this new Chrysanthemum are stable and reproduced true to type in successive generations.

BRIEF SUMMARY OF THE INVENTION

The cultivar Anastasia Yellow has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Anastasia Yellow'. These characteristics in combination distinguish 'Anastasia Yellow' as a new and distinct cultivar:

1. Large quilled spider double-type inflorescences with yellow-colored ray florets; typically grown as a disbudded type with a single inflorescence per flowering stem.
2. Numerous ray florets and very few disc florets; disc florets typically inconspicuous.
3. Dark green-colored foliage.
4. Strong and upright flowering stems.

5. Low number of lateral branches which reduces the amount of disbudding required.
6. Short response time.
7. Excellent postproduction longevity.

Plants of the new Chrysanthemum are most similar to plants of the parent cultivar Anastasia. In side-by-side comparisons conducted by the Inventor in 's-Gravenzande, The Netherlands, plants of the new Chrysanthemum differed primarily from plants of the cultivar Anastasia in ray floret coloration as plants of the cultivar Anastasia had white-colored ray florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the first sheet comprises a side perspective view of a typical flowering stem of 'Anastasia Yellow'.

The photograph at the bottom of the second page comprises a close-up view of the upper and lower surfaces of typical leaves of 'Anastasia Yellow'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in 's-Gravenzande, The Netherlands, under commercial practice in a glass-covered greenhouse. Plants were initially given long day/short night treatments followed by short day/long night treatments to induce flower initiation and development. Average day and night temperatures were 18 and 19° C., respectively. Plants were not pinched and were grown as single-stem disbud types.

Botanical classification: *Chrysanthemum×morifolium* cultivar Anastasia Yellow.

Commercial classification: Quilled spider double-type Chrysanthemum typically grown as a disbudded cut flower.

Parentage: Naturally-occurring whole plant mutation of *Chrysanthemum×morifolium* cultivar Anastasia, disclosed in U.S. Plant Pat. No. 13,550.

Propagation:

*Type.*—Terminal tip cuttings.

*Time to initiate roots, summer.*—About 10 days at 20° C.

*Time to initiate roots, winter.*—About 14 days at 20° C.

*Root description.*—Fine, fibrous and well-branched.

Plant description:

*Appearance.*—Herbaceous quilled spider double-type cut Chrysanthemum; typically grown as a single-stem and as a disbudded type with one single inflorescence per flowering stem. Upright and strong flowering stems.

*Growth rate.*—Moderate; moderately vigorous.

*Crop time.*—For cut flowers, about 78 and 117 days are required to produce flowering stems during the summer and winter, respectively.

*Flowering stem description.*—Length: About 70 to 80 cm. Diameter, at apex: About 6.5 mm. Strength: Strong. Aspect: Upright. Branching habit: Plants are typically grown as single stems, but if pinched, will develop 8 to 12 lateral stems. Color: 146B.

*Foliage description.*—Arrangement: Alternate. Quantity of leaves per main stem: About 12 to 15. Length: About 10 to 13 cm. Width: About 6 to 9 cm. Apex: Acute. Base: Acute to obtuse. Margin: Palmately lobed. Texture, upper and lower surfaces: Rough; pubescent. Petiole length: About 3 to 4 cm. Color: Young and fully expanded foliage, upper surface: 147A. Young and fully expanded foliage, lower surface: 147B. Venation, upper and lower surfaces: 147B. Petiole: 147B.

Inflorescence description:

*Appearance.*—Quilled spider double-type inflorescence form. Inflorescences borne on terminals, arising from leaf axils. Ray and disc florets develop acropetally on the receptacle.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about seven weeks later.

*Postproduction longevity.*—Inflorescences will maintain good substance and form for about 3.5 weeks after harvesting.

*Quantity of inflorescences per flowering stem.*—Grown as a disbud type, all lateral inflorescences are removed and only the terminal inflorescence develops. If lateral inflorescences are not removed, about 8 to 11 inflorescences per flowering stem will develop.

*Inflorescence size.*—Diameter: Large, about 11 to 14 cm. Depth (height): About 4 to 5 cm. Diameter of disc: About 1.4 cm; inconspicuous.

*Inflorescence buds.*—Length: About 1 to 1.5 cm. Diameter: About 1.2 to 1.5 cm. Shape: Oblate. Color: Close to 146A.

*Ray florets.*—Length, fully developed: About 6.5 to 7.5 cm. Width, fully developed: About 7 to 8 mm. Shape: Fused, tubular; quilled. Texture: Smooth, glabrous. Number of ray florets per inflorescence: About 350. Color: When opening, upper and lower surfaces: 13C. Mature, upper and lower surfaces: 12C; color fading to 2D with 8C towards the base with subsequent development.

*Disc florets.*—Shape: Oblong, tubular. Length: About 5 mm. Width: About 1 mm. Number of disc florets per inflorescence: Few, about 10; inconspicuous. Color: Immature: Close to 154D. Mature: Towards apex, 13A; towards base, close to 150D.

*Peduncles.*—Length, terminal peduncle: About 3 to 4 cm. Length, fourth peduncle: About 4 to 5 cm. Diameter: About 6 to 7 mm. Texture: Pubescent. Color: 146B.

*Reproductive organs.*—Androecium: Present on disc florets only. Anther color: 15B. Amount of pollen: Moderate. Pollen: 16B. Gynoecium: Present on both ray and disc florets. Stigma length: About 5 mm. Stigma width: About 0.5 mm. Stigma color: Towards apex, 9C; towards base, close to 155C.

*Seed/fuit.*—Seed and fruit production has not been observed.

Disease/pest resistance: Resistance to known Chrysanthemum pathogens and pests has not been observed on plants of the new Chrysanthemum.

It is claimed:

1. A new and distinct cultivar of Chrysanthemum plant named 'Anastasia Yellow', as illustrated and described.

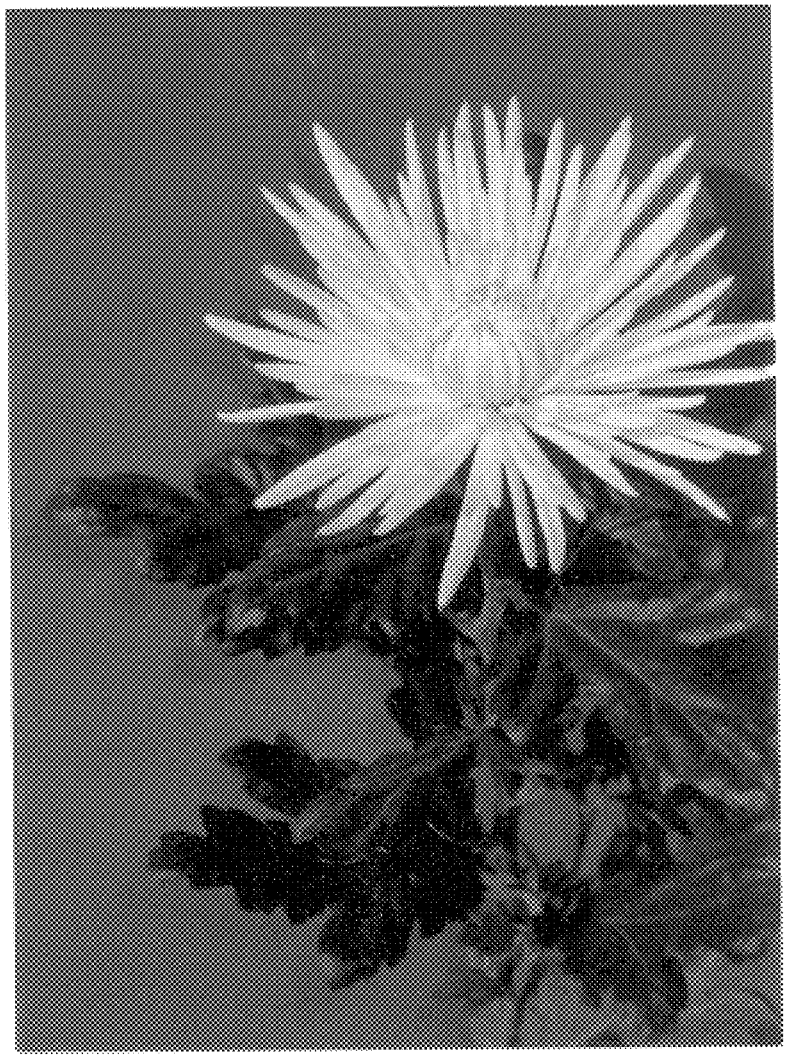
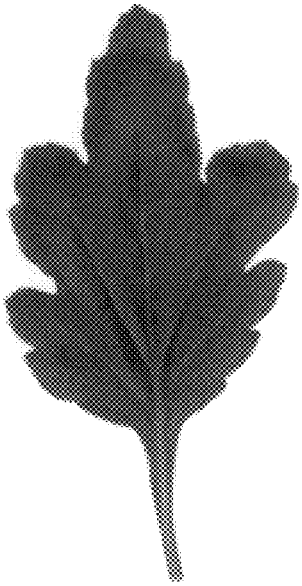
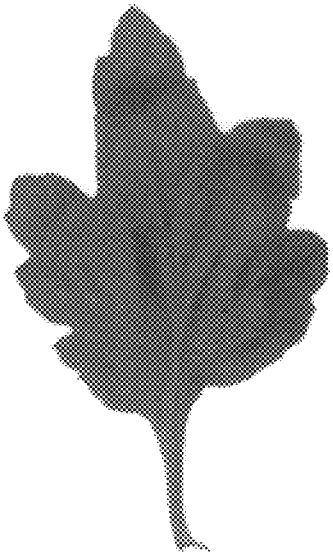

* * * * *